United States Patent
Blum et al.

(10) Patent No.: US 7,078,393 B2
(45) Date of Patent: Jul. 18, 2006

(54) METHOD OF PRODUCING 1-HYDROXY-1,1-DIPHOSPHONIC ACID COMPOUNDS

(75) Inventors: Helmut Blum, Düsseldorf (DE); Wolfgang Greb, Düsseldorf (DE); Yurii Pustovit, Kyiv (UA); Gerd-Volker Röschenthaler, Bremen (DE)

(73) Assignee: EUCRO European Contract Research GmbH & Co. KG, Neuss (DE)

( * ) Notice: Subject to any disclaimer, the term of this patent is extended or adjusted under 35 U.S.C. 154(b) by 296 days.

(21) Appl. No.: 10/471,828

(22) PCT Filed: Mar. 12, 2002

(86) PCT No.: PCT/EP02/02676

§ 371 (c)(1),
(2), (4) Date: Sep. 15, 2003

(87) PCT Pub. No.: WO02/76515

PCT Pub. Date: Mar. 10, 2002

(65) Prior Publication Data

US 2004/0087554 A1    May 6, 2004

(30) Foreign Application Priority Data

Mar. 22, 2001 (DE) .................. 101 14 352

(51) Int. Cl.
*A61K 31/66* (2006.01)
*C07F 9/28* (2006.01)

(52) U.S. Cl. ..................... 514/107; 562/13
(58) Field of Classification Search .......... 562/13; 514/107
See application file for complete search history.

(56) References Cited

U.S. PATENT DOCUMENTS 4,608,368 A * 8/1986 Blum et al. .................. 514/107

OTHER PUBLICATIONS

Marc Lecouvey et al., A mild and efficient one-pot synthesis of 1-hydroxymethylene-1,1-bisphosphonic acids. Preparation of new tripod ligands, "Tetrahedron Letters 42 pp. 8475-8478, 2001".*

* cited by examiner

*Primary Examiner*—Johann Richter
*Assistant Examiner*—Ebenezer Sackey
(74) *Attorney, Agent, or Firm*—Gudrun E. Huckett

(57) ABSTRACT

In a method for preparing 1-hydroxy-1,1-diphosphonic acid compounds of the general formula I and/or of their pharmacologically compatible salts

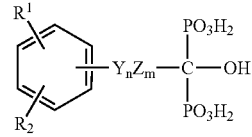
(I)

a compound of the formula II

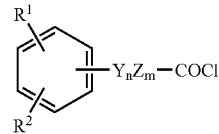
(II)

is reacted with a compound $P(OSiR^5{}_3)_{3-p}R^6{}_p$ and the reaction product is hydrolyzed.

10 Claims, No Drawings

METHOD OF PRODUCING 1-HYDROXY-1,1-DIPHOSPHONIC ACID COMPOUNDS

BACKGROUND OF THE INVENTION

The present intention relates to a method for preparing 1-hydroxy-1,1-diphosphonic acid compounds.

The concept of "drug targeting", i.e., the targeted accumulation of medicaments at the location of desired action, is a strategy that has been used for some time in medicine and the pharmaceutical industry. Of special interest in this connection is the use of cytostatic agents, for example, of N lost derivatives such as chlorambucil (4-(4-bis-(2-chloroethyl) amino)benzene butanoic acid) coupled to special alkane diphosphonic acids. As a result of the high affinity of the diphosphonic acids to apatite of the bone structure, a targeted organ specificity is obtained. The compound class of such 1-hydroxy-1,1-diphosphonic acid compounds, their manufacture as well as their use as pharmacological compositions is described in European patent EP 0 170 896 B1.

According to EP 0 170896B1,1-hydroxy-1,1-diphosphonic acid compounds are produced from carboxylic acid chlorides by reaction with $H_3PO_3$ in the presence of a dehydrating agent in yields of approximately 50%.

For the pharmaceutical use, the 1-hydroxy-1,1-diphosphonic acid compounds must have a high degree of purity; also, high yields of the manufacturing processes are desirable.

Moreover, the compounds must have a certain solubility for pharmaceutical use. The solubility of these compounds is in itself very low; moreover, the compounds are partially hydrolytically unstable. An improved solubility and thus a higher concentration in the pharmacological composition can be obtained, for example, by employing salts of the corresponding compounds. According to the prior art, the corresponding salts are produced by neutralization with the equivalent amount of the base. In this connection, the isolation of the salts is realized by precipitation with organic solvents, for example, alcohols, by crystallization, or by solvent evaporation from the (partially) neutralized solution. However, discolored products are often obtained with these methods; also, the products partially decompose resulting in a reduced yield; moreover, the partially uncharacterized decomposition products are undesirable in particular in connection with the use in the pharmaceutical sector.

For the isolation of the salts, it is proposed in DE 198 20 974 A1 to isolate the salts by means of freeze-drying.

SUMMARY OF THE INVENTION

The present invention has the object to provide a method that is improved in comparison to the prior art for preparing 1-hydroxy-1,1-diphosphonic acid compounds, which method provides these compounds, for example, in higher yields.

Object of the present invention is a method for preparing 1-hydroxy-1,1-diphosphonic acid compounds of the general formula I and/or of their pharmacologically compatible salts

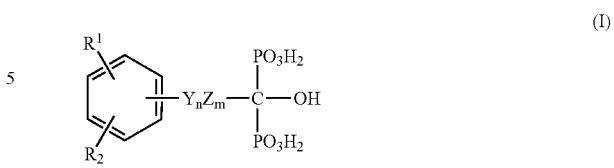

wherein
$R^1$ is hydrogen, OH, $NO_2$, Cl, F, Br, $C_1$–$C_6$ alkyl that can also be substituted by halogen, amino, and/or aminoalky, $C_1$–$C_6$ alkoxy, aryl, heteroaryl, a group $NR^3R^4$ in which $R^3$ and $R^4$ can be identical or different and represent hydrogen, $C_1$–$C_6$alkyl, halogen-substituted alkyl, hydroxy-$C_1$–$C_6$ alkyl,
$R^2$ is hydrogen, halogen, amino that can also be substituted, $C_1$–$C_6$ alkyl that can also be substituted by halogen, amino, and/or aminoalky, $C_1$–$C_6$ alkoxy, aryl, heteroaryl,
Y O, S, or NH,
Z $C_1$–$C_5$ alkylene that can be substituted by amino groups,
m and n are 0 or 1, under the condition that, when n=1 then also m=1, wherein a compound of the formula II

wherein $R^1$, $R^2$, Y, Z, m, and n are defined as above, is reacted with a compound of the formula III

wherein
$R^5$ is a $C_1$–$C_4$ alkyl group,
$R^6$ is a $C_1$–$C_6$ alkoxy group,
p is 0, 1, or 2,
wherein the reaction product is hydrolyzed in a known way and optionally reacted to the salts.

The method according to the invention enables the preparation of 1-hydroxy-1,1-diphosphonic acid compounds in high yields and in such a purity that the products can also be used in pharmacological compositions. Also, a further reaction to form the easily soluble salts is possible.

According to the invention, $R^1$ in the compounds of the formula I is hydrogen, OH, $NO_2$, Cl, F, Br, $C_1$–$C_6$ alkyl that can also be substituted by halogen, amino, and/or aminoalky, $C_1$–$C_6$ alkoxy, aryl, heteroaryl, a group $NR^3R^4$ in which $R^3$ and $R^4$ can be identical or different and represent hydrogen, $C_1$–$C_6$ alkyl, halogen-substituted alkyl, hydroxy-$C_1$–$C_6$ alkyl. In a preferred embodiment, $R^1$ is a $NR^3R^4$ group in which $R^3$ and $R^4$ are identical and represent a halogen-substituted $C_1$–$C_6$ alkyl group, preferably, a group —$CH_2$— $CHR^7Cl$, wherein $R^7$ is hydrogen or a methyl group, preferably, hydrogen.

Preferred halogen substituents for $R^2$ are fluorine, chlorine, or bromine. Preferred alkyl moieties or alkoxy moieties for $R^2$ have not more than 5, in particular, not more than 3, C atoms; preferably, they are methyl or ethyl groups. The alkyl moieties or alkoxy moieties can optionally be substituted, for example, by one or several amino groups. $R^2$ can also be an amino group, optionally substituted. In a preferred embodiment, $R^1$ is hydrogen, a methyl, methoxy or nitro group.

Relative to the molecule part that is bonded to the aromatic ring by Y, the moiety $R^1$ can be in o, m or p position. When the moiety $R^1$ is an amino group, this molecule part is preferably in the p position wherein $R^1$ is then a so-called N lost group.

According to the invention, m and n can be 0 or 1, but under the condition that when n=1, i.e., one of the moieties O, S, or NH is present, then also m=1. In a preferred embodiment, n=0, i.e, the moiety Y is not present. In this configuration, it is also possible that n=0.

It is especially preferred that n=0 and m=1, i.e., the alkylene group Z is directly bonded to the aromatic ring. This linear or branched or optionally substituted moiety Z contains preferably not more than 5 C atoms, in particular, not more than 3 C atoms, wherein unbranched C chains are preferred. As an example of possible substituents on Z an amino group should be mentioned. Preferred substituents for Z are the following:

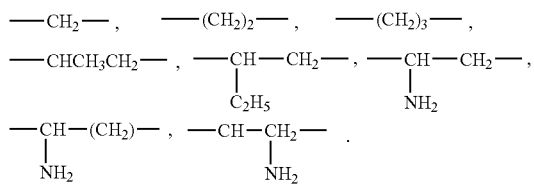

A preferred embodiment of the formula I is 4-(4-(bis-(2-chloroethyl)amino)benzene)-1hydroxybutane-1,1-diphosphonic acid that is referred to, for short, as "CAD" (chlorambucil coupled to 1-hydroxy-1,1-diphosphonic acid).

For preparing the compounds of the formula I, according to the invention in a first reaction step as a starting material the carboxylic acid derivatives of the formula II are reacted with a phosphorylating agent of the formula II. The compounds of the formula II and formula III are preferably reacted in approximately stoichiometric amounts. Stoichiometric means that the starting compounds are reacted approximately in a molar ratio of 1:2 when the compound of the formula I does not contain an amino group. The molar ratio of the compounds of the formula II to the compounds of the formula III is preferably approximately 1:3 when the compound of the formula II contains an amino group.

In order to achieve excellent mixing of the reaction partners, the reaction mixture is preferably stirred.

The reaction of the compounds of the formula II with the compound of the formula III can be carried out within a wide temperature range of −30° C. to 50° C. Preferably, the reaction is carried out at a temperature from 10 to 30° C. Temperatures significantly above room temperature are not preferred because of the formation of undesirable byproducts.

In the method according to the invention, it was found to be advantageous to dissolve the compound of the formula II first in a suitable organic solvent or to suspend it therein and to add the compound of the formula III, either as a pure compound or also in a dissolved or suspended form. The solvent for dissolving the compounds of the formula II and formula III can be polar or non-polar organic solvents such as toluene, benzene, chlorobenzene, pentane, hexane, hexane, heptane, petroleum ether, diethyl ether, tetrahydrofurane After the addition of the compounds of the formula III, it is preferred to allow the reaction mixture to react for some time. For this purpose, the temperature can be optionally increased somewhat, wherein an after reaction at room temperature is preferred.

The reaction product obtained in the first method step by reaction of the compounds of the formulas II and III, can be isolated by known methods after completion of the reaction or can be directly further reacted to the diphosphonic acid, i.e., can be hydrolyzed. Preferably, before further reactions are carried out, volatile reaction (by)products are removed in vacuum.

The hydrolysis of the reaction product obtained in the first method step is carried out by known methods. Preferably, the reaction product is dissolved in one of the above-mentioned organic solvents and water is added, optionally with stirring, and the compound of the formula I is formed.

The compound of the formula I can be isolated as is known in the art and, if required, can be purified in that the generally insoluble reaction product is filtered to remove the solvent and, optionally, is washed with solvent.

For use in pharmacological compositions, the compounds of the formula I are preferably used in the form of their soluble salts. Partial salts, in which only a part of the four of the acidic protons are replaced by other cations, as well as complete salts as well as mixtures of different salts as well as mixtures of the free acids with salts can be used. Examples of pharmacologically compatible salts are alkali, earth alkali and/or ammonium salts, such as sodium, potassium, magnesium, ammonium, and substituted ammonium salts. Preferred are essentially neutral-reacting salts whose pH value in aqueous solution is between approximately 5 and 9. Especially preferred are partially neutralized salts such as monosodium, disodium, and trisodium salts, and completely neutralized sodium salts of the compounds of the formula I.

The neutralization of the compounds of the formula I can be carried out as is known in the art by reaction with the corresponding bases, as is described, for example, in EP 0 170 896 A1 and in DE 198 20 974 A1. Preferably, the aqueous solutions of the corresponding alkali, earth alkali, and ammonium compounds, such as sodium, potassium, magnesium, ammonium and substituted ammonium compounds, are used, wherein an aqueous sodium hydroxide solution is preferred as a base. Usually, the 1-hydroxy-1,1-diphosphonic acid compounds are reacted with equivalent amounts of the base; for example, when preparing a tetrasodium salt, the base is added in a four-fold molar ratio relative to 1-hydroxy-1,1-diphosphonic acid compounds. Correspondingly, when preparing the disodium salt, a two-fold molar ratio of the base is used. It was found to be advantageous when the 1-hydroxy-1,1-diphosphonic acid compounds are added to the cold—preferably from 0° C. to room temperature—solution of the base. In a preferred embodiment, the reaction is carried out in an $O_2$-free atmosphere and the solution is subsequently allowed to warm to room temperature. The neutralization with alkali hydride is also possible.

The neutralization can be realized also by adding the 1-hydroxy-1,1-diphosphonic acid compound to an aqueous cold sodium carbonate solution, wherein equivalent amounts or up to twice the amount of sodium carbonate ($Na_2CO_3$) is used. A further possibility of preparing the salts resides in the use of ion exchangers.

In another preferred embodiment, for the preparation of the alkali salts, the compound of the formula I is reacted with a corresponding alkali acetate, in particular, sodium acetate. The reaction is preferably carried out at room temperature.

The product which is obtained from the (partial) neutralization can be directly further reacted after removal of the volatile reaction products; a difficult isolation is generally not required.

Compounds of the formula I in which $R^1$ is hydrogen, Me, OMe, $NH_2$, $NO_2$ and $R^2$ is hydrogen, Z is a propylene group, n is 0, and m is 1, are new.

Accordingly, a further object of the present intention is a compound of the following formula IV

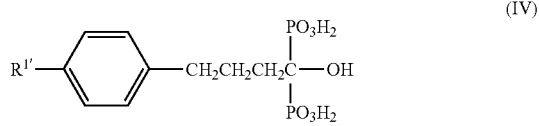

wherein $R^{1'}$=H, Me, OMe, $NH_2$, $NO_2$ and a compound of the formula V

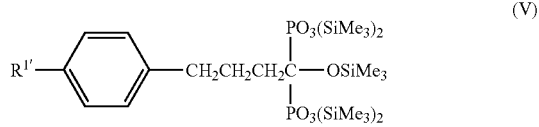

wherein $R^{1'}$=H, Me, OMe, $NH_2$, $NO_2$.

DESCRIPTION OF REFERRED EMBODIMENTS

EXAMPLES

Example 1

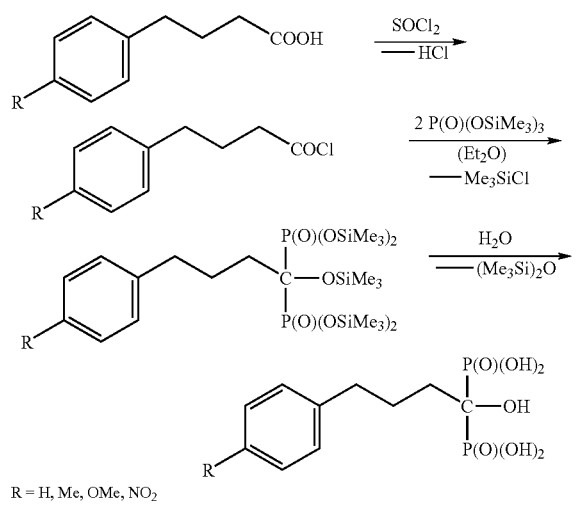

R = H, Me, OMe, $NO_2$ 1.1 Preparation of the Acid Chlorides with $SOCl_2$ According to Methods Known from the Literature The required preparations for working under exclusion of moisture and oxygen were carried out (dry diethyl ether, dry and oxygen-free nitrogen (gas) as an inert gas atmosphere).

1.2 Preparation of Diphosphonic Acids via Persilylated Derivatives (for R=H, Me, OMe, $NO_2$)

6.7 ml (appr. 20 mmol) of tris(trimethylsilyl)phosphite (Hata, T.; Sekine, M; *J. Am. Chem. Soc.* 96 (1974) 7363; Sekine, M; Okimoto, K; Yamada, K.: *J. Org. Chem.* 46 (1981) 2097) were added to a solution of the acid chloride (appr. 10 mmol) in 30 ml of diethyl ether, the mixture was stirred for 1–2 hours, and the volatile components removed at 80–90° C. in water-jet pump vacuum (20 mbar). NMR ($Et_2O$) of the persilylated derivatives: $^{31}P$: e.g. δ=3.42 (R=H), 3.65 (R=$NO_2$).

Water (10 ml) was added to the residue, the mixture heated under stirring for 1 h at 80–90° C. and then dried in vacuum (0.1 mbar). The residue was then treated with 10–15 ml diethyl ether, the precipitated material was filtered, washed with a small amount of diethyl ether, and dried (for R=H, Me, $NO_2$). In the case of R=OMe, the residue with treated with ethyl acetate, washed with a minimum amount of ethyl acetate, and dried. For R=$NO_2$ a diphosphonic acid diethyl ether complex (1:1) was obtained that was converted to the pure acid by heating for 2 h at 80–90° C. while pumping at 0.1 mbar. Melting point diphosphonic acid R=H ($C_{10}H_{16}O_7P_2$, 310.18) 183–185° C. (yield 75% relative to the corresponding acid chloride); NMR: $^1H$ (DMSO-$d_6$) δ=1.86 (m, 4H, $CH_2CH_2CH_2$), 2.51 (m, 2H, $CH_2CO$), 7.18 (m, 5H, Ph), 10.20 (5H, br, OH); $^{31}P$ (DMSO-$d_6$) δ=21.63 ($^3J_{PH}$=14.0 Hz). MS: (FAB, m/z %) FAB$^+$311 ($M^+$+H), FAB$^-$309 ($M^-$–H); R=Me ($C_{11}H_{18}O_7P_2$, 324.20) 175–177° C. (71%); NMR: $^1H$ (DMSO-$d_6$) δ=1.86 (m, 4H, $CH_2CH_2CH_2$), 2.24 (3H, Me), 2,44 (2H, $CH_2CO$), 7.04 (m, 4H, Ph), 9.06 (5H, br, OH); $^{31}P$ (DMSO-$d_6$) δ=21.35 ($^3J_{PH}$=13.90 Hz). MS: (FAB, m/z %): FAB$^+$325 ($M^+$+H), FAB$^-$323 ($M^-$–H); R=OMe ($C_{11}H_{18}O_8P_2$, 340.20) 173–175° C. (67%); NMR: $^1H$ (DMSO-$d_6$) δ=1.88 (m, 4H, $CH_2CH_2CH_2$), 2.54 (2H, $CH_2CO$), 3.75 (3H, OMe), 6.90 (2H, AB, Ph), 7.10 (2H, AB, Ph), 10.15 (5H, br, OH); $^{31}P$ (DMSO-$d_6$) δ=21.22 ($^3J_{PH}$=13.0 Hz). MS: (FAB, m/z %): FAB$^+$341 ($M^+$+H), FAB$^-$339 ($M^-$–H); R=$NO_2$ 172–174° C. (70%) ($C_{10}H_{15}NO_9P_2$, 355.17); NMR: $^1H$ (DMSO-$d_6$) δ=1.90 (m, 4H, $CH_2CH_2CH_2$), 2.69 (2H, $CH_2CO$), 6.50 (2H, AB, Ph), 8.15 (2H, AB, Ph), 10.37 (5H, br, OH); $^{31}P$ (DMSO-$d_6$) δ=21.15 ($^3J_{PH}$=13.0 Hz). MS: (FAB, m/z %): FAB$^+$356 ($M^+$+H), FAB$^-$354 ($M^-$–H).

Example 2

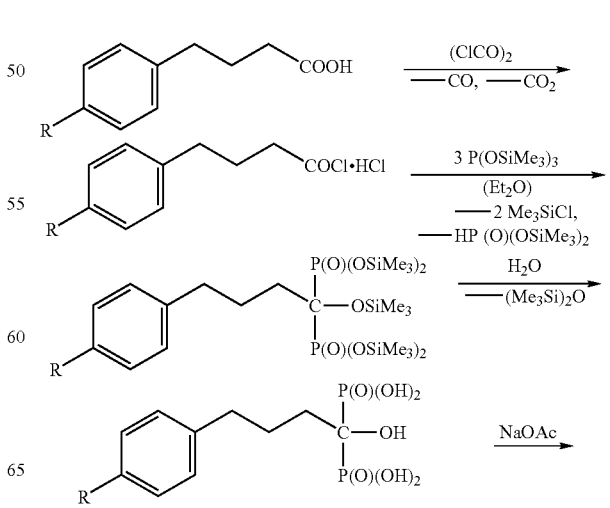

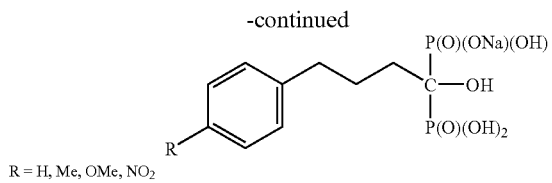

R = H, Me, OMe, NO₂

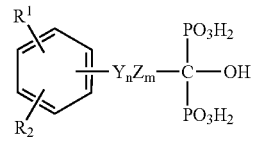

2.1 Preparation of Chlorambucil Hydrochloride $C_{14}H_{19}Cl_4NO$ [359.24] according to Firestone, R. A. et al., J. Med. Chem. 1984, 27 1037

Oxalylchloride 5.2 ml (60 mmol) was added to a stirred solution of 1.82 g (appr. 6 mmol) of chlorambucil in 30 ml of methylene chloride at 0° C. together with a drop of DMF (dimethylformamide). The mixture was stirred at the same temperature for 30 minutes, then for 1.5 h at room temperature, and then dried under water-jet pump vacuum (20 mbar) in a water bath (40–50° C.), then at the same temperature in vacuum (0.1 mbar) The yield of chlorambucil hydrochloride 2.16 g (slightly yellow solid) was quantitative.

2.2 Preparation of Persilylated Chlorambucil Diphosphonic Acid $C_{29}H_{63}Cl_2NO_7P_2Si_5$[811.12]

Tris(trimethylsilyl)phosphite 6.0 ml (appr. 18 mmol) was added under stirring to a suspension of the acid chloride hydrochloride (appr. 6 mmol) in 30 ml diethyl ether at room temperature, stirred for 1–2 h (after 30 to 60 minutes the suspension disappeared) and the volatile components were removed for 2–3 hours at 80–90° C. (0.1 mbar). The residue was an oily liquid. Yield 4.9 g, almost quantitative. NMR ($Et_2O$): $^{31}P$:δ=4.09.

2.3 Preparation of Chlorambucil Diphosphonic Acid $C_{14}H_{23}Cl_2NO_7P_2$ [450.19]

To the oily liquid of 2.2 6 ml water was added. The reaction mixture was allowed to rest for 3–4 h until the formed solid disappeared, then dried at 45–50° C. in vacuum (0.1 mbar). The remaining residue was heated in ethyl acetate to reflux, then filtered, and dried in vacuum (0.1 mbar) at 45–50° C. Melting point 155–165° C., yield 2.7 g, almost quantitative. NMR: $^1H$ (DMSO-$d_6$) δ=1.80 (m, 4H, $CH_2CH_2CH_2$), 2.38 (m, 2H, $CH_2CO$), 3.66 (8H, $CH_2$) 6.66 (2H, AB, Ph), 6.98 (2H, AB, Ph), 9.50 (5H, br, OH); $^{31}P$ (DMSO-$d_6$) δ=21.48 ($^3J_{PH}$=14.0 Hz). MS: (FAB, m/z) FAB⁻ 448 (M⁻–H).

2.4 Preparation of Sodium Chlorambucil Diphosphonate $C_{14}H_{22}Cl_2NNaO_7P_2$ [472.17]

Chlorambucil diphosphonic acid (2.25 g, appr. 5 mmol) of 2.3 were slurried in 6 ml water and 0.95 g (7 mmol) sodium acetate was added and allowed to react while constantly stirring for 15–20 hours. The white product was filtered, washed 3 times with 1 ml water and 3 times with 5 ml ethanol, first dried in air, then in vacuum at 40° C. Yield 1.88 g (80%). NMR: $^1H$($CF_3COOD$): δ=2.20 (m, 4H, $CH_2CH_2CH_2$), 2.80 (m, 2H, $CH_2CO$), 3.42 (2H, $CH_2$), 3.80 (2H, $CH_2$), 4.14 (4H, 2 $CH_2$), 7.54 (4H, br, Ph); $^{31}P$ ($CF_3COOD$): δ=22.38 ($^3J_{PH}$=14.0 Hz). MS: (FAB, m/z %) FAB⁺23 (Na⁺); FAB⁻470 (M⁻–H).

What is claimed is:

1. A method for preparing 1-hydroxy-1,1-diphosphonic acid compounds of the general formula I and/or of their pharmacologically compatible salts

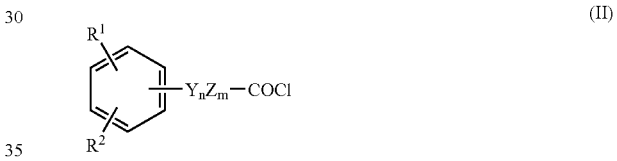

wherein
R¹ is hydrogen, OH, NO₂, Cl, F, Br, $C_1$–$C_6$ alkyl optionally substituted by halogen, amino, and/or aminoalky, $C_1$–$C_6$ alkoxy, aryl, heteroaryl, a group NR³R⁴ in which R³ and R⁴ are identical or different and represent hydrogen, $C_1$–$C_6$ alkyl, halogen-substituted alkyl, hydroxy-$C_1$–$C_6$ alkyl, R² is hydrogen, halogen, amino that is optionally substituted, $C_1$–$C_6$ alkyl optionally substituted by halogen, amino, and/or aminoalky, $C_1$–$C_6$ alkoxy, aryl, heteroaryl, Y O, S, or NH, Z $C_1$–$C_5$ alkylene optionally substituted by amino groups, m and n are 0 or 1, under the condition that when n=1 then also m=1, the method comprising the steps of:

a) reacting a compound of the formula II

wherein R¹, R², Y, Z, m, and n are defined as above, with a compound of the formula III $$P(OSiR^5_3)_{3-p}R^6_p \quad (III)$$

wherein R⁵ is a $C_1$–$C_4$ alkyl group; R⁶ is a $C_1$–$C_6$ alkoxy group; p is 0, 1, or 2; and b) hydrolyzing the reaction product of step a).

2. The method according to claim 1, further comprising the step of reacting the hydrolyzed product to the pharmacologically compatible salts.

3. The method according to claim 1, wherein the compound of the formula I is 4-(4-(bis-(2-chloroethyl)amino) benzene)-1-hydroxybutane-1,1-diphosphonic acid.

4. The method according to claim 1, wherein p is 0 in the formula III.

5. The method according to claim 1, wherein in step a) the compounds of the formula II and of the formula III are reacted in approximately stoichiometric amounts.

6. The method according to claim 1, further comprising the step of preparing the pharmacologically compatible salts, wherein the compounds of the formula I are neutralized or partially neutralized with aqueous solutions of the corresponding alkali, earth alkali, and ammonium compounds.

7. The method according to claim 6, wherein sodium, potassium, magnesium, ammonium, and substituted ammonium compounds are used.

8. The method according to claim 6, wherein alkali acetate is used.

9. A compound of the formula (IV)
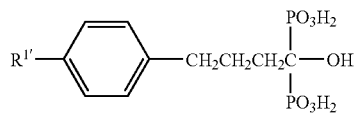
wherein $R^{1'}$=H, Me, OMe, $NH_2$, $NO_2$.
10. A compound of the formula (V)
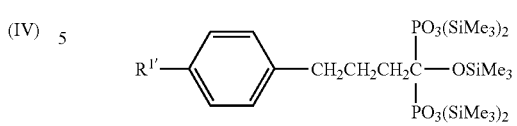
wherein $R^{1'}$=H, Me, OMe, $NH_2$, $NO_2$.
* * * * *